United States Patent [19]

Kelman

[11] Patent Number: 4,563,779
[45] Date of Patent: Jan. 14, 1986

[54] CORNEAL IMPLANT AND METHOD OF MAKING THE SAME

[76] Inventor: Charles D. Kelman, North Shore Towers, 269 Grand Central Pkwy, Bldg. 3, Floral Park, N.Y. 11005

[21] Appl. No.: 574,677

[22] Filed: Jan. 27, 1984

[51] Int. Cl.$^4$ ............................ A61F 1/16; A61F 1/24
[52] U.S. Cl. ...................................... 623/5; 128/1 R; 128/303 R; 128/334 R
[58] Field of Search ............. 3/13, 1; 128/305, 334 R, 128/303 R, 1 R

[56] References Cited

U.S. PATENT DOCUMENTS

| | | | |
|---|---|---|---|
| 2,714,721 | 8/1955 | Stone, Jr. ............................... | 3/13 X |
| 2,754,520 | 7/1956 | Crawford, Jr. ......................... | 3/13 |
| 4,077,411 | 3/1978 | Ward .................................. | 128/303 R |
| 4,346,482 | 8/1982 | Tennant et al. ......................... | 3/13 |

OTHER PUBLICATIONS

"Fluid-Barrier Procedure": Artificial Corneal Endothelium Tested, JAMA, vol. 198, No. 6, Nov. 7, 1966, pp. 40–41.
"Optical Properties of Buried Corneal Silicone Prostheses" by David Miller et al., American Journal of Ophthalmology, vol. 66, No. 4, Oct. 1968, pp. 633–640.

*Primary Examiner*—Ronald L. Frinks
*Attorney, Agent, or Firm*—Henry Sternberg; Bert J. Lewen

[57] ABSTRACT

A corneal implant and method of making the same utilizes a corneal plug removed from an eye, frozen solid, and centrally bored to, but not through, its Bowman's or its Descemet's membrane. An artificial plug which is optically clear is inserted in the bore of the corneal plug and attached thereto. The corneal plug with the artificial plug therein is thereafter implanted in a corresponding opening in the cornea of the patient's eye providing a transparent window free of fluid leakage.

21 Claims, 6 Drawing Figures

CORNEAL IMPLANT AND METHOD OF MAKING THE SAME

This invention relates to corneal implants and to methods of making the same.

The healthy cornea of a human eye is approximately 0.5 mm thick in the central region thereof and approximately 1.0 mm thick in the peripheral region thereof. The cornea comprises substantially parallel relatively compacted layers of tissue. The central, cornea portion of the eye, is transparent and relatively free of fluid. Outwardly of the cornea, the fibers making up the tissue of the sclera are more randomly arranged as distinguished from the aforesaid parallel layers and as a result the sclera which surrounds the cornea is not transparent. The posterior surface of the cornea comprises an endothelial layer which, when normal, functions as a fluid pump to pump fluid out of the central region of the cornea so as to maintain the latter relatively dry. The endothelial layer does not regenerate and thus when it is diseased, scratched or otherwise injured, it no longer functions to withdraw fluid from the cornea, permitting the fluid to build up between the layers of the central corneal region causing the latter to become thicker, irregular, and less transparent, i.e., cloudy.

The anterior surface of the cornea is covered by an epithelial layer. This is a protective layer of tissue which does regenerate if injured and which has a base surface known as Bowman's membrane. Bowman's membrane is a very thin (less than 0.1 mm thick), but very strong, membrane which acts as a protective outer cover for the cornea.

In corneal transplant surgery, it is known to cut a cylindrical plug from the central corneal region of the afflicted eye. An identically shaped plug of the central corneal region is then cut from a donor eye. The plug cut from the donor eye is placed into the opening remaining in the afflicted eye and sutured thereto. The two will then grow together. Since the region in question is normally not vascular, antibodies which might result in rejection of foreign tissue are normally not supplied to the region, and rejection is therefore unlikely.

Unfortunately, there are many more patients suffering from disease or injury of the cornea than there are donor eyes available for such transplants. Numerous attempts have been made to solve this problem. However, these generally have not proven successful. According to one such method, a plug is cut out of the central corneal region and a plastic plug is inserted into the resulting opening. The plug is provided with flanges at the opposite ends thereof in an effort to prevent fluid leakage. It has as yet, however, generally been impossible to achieve an adequate seal with plastic plugs.

One prior corneal implant uses an undesirably wide artificial implant holding member for supporting the plug in the cornea.

It is an object of the invention, therefore, to provide a new and improved corneal implant which avoids one or more of the above-mentioned disadvantages and limitations of prior such implants.

It is another object of the invention to provide a new and improved corneal implant which provides a satisfactory seal with the patient's eye to prevent fluid leakage.

It is another object of the invention to provide a new and improved method of making a corneal implant which avoids one or more of the disadvantages and limitations of prior such methods.

It is another object of the invention to provide a new and improved method of making a corneal implant which can be implanted in a patient's eye in such a manner as to prevent fluid leakage therefrom.

It is still another object of the invention to provide a new and improved method of making a corneal implant for a patient's eye using a membrane previously removed from the eye of an animal.

It is still another object of the invention to provide a new and improved corneal implant for a patient's eye incorporating a membrane previously removed from the eye of an animal.

In accordance with the present invention, a corneal implant comprises a corneal plug removed from a donor eye and having a Bowman's membrane, a posterior surface spaced from the Bowman's membrane and a bore therein extending substantially to Bowman's membrane from the posterior surface. The implant also includes an optically clear artificial plug having dimensions to fit the bore and disposed in the bore.

Also in accordance with the invention, a method of making a corneal implant comprises removing from a donor eye a corneal plug having Bowman's membrane and a posterior surface. The method also includes the steps of solidifying the corneal plug, cutting a bore in the solidified corneal plug from the posterior surface substantially to Bowman's membrane and disposing in the bore of the solidified corneal plug an optically clear artificial plug having dimensions to fit the bore, and attaching the artificial plug to the corneal plug.

For a better understanding of the present invention together with other and further objects thereof, reference is made to the following description, taken in connection with the accompanying drawings, and its scope will be pointed out in the appended claims.

Referring now to the drawings.

Figure 1:
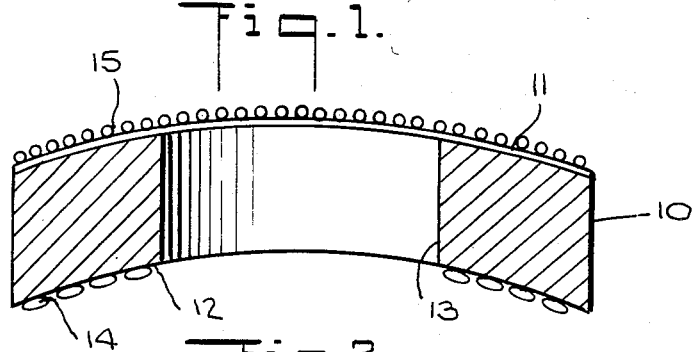
FIG. 1 is a sectional view of a corneal plug utilized in an embodiment of the present invention.

Referring now more particularly to FIG. 1 of the drawings, a corneal implant comprises a corneal plug 10 having Bowman's membrane 11 and a posterior surface 12 and removed from a donor eye, preferably a patient's eye, and having a bore 13 therein extending substantially to Bowman's membrane from the posterior surface 12. Endothelial layer 14 and epithelial layer 15 are represented diagrammatically. The corneal plug 10 having had the clouded central portion thereof bored out is, of course, transparent, i.e. optically clear in the region defined by the bore and Bowman's membrane capping the bore.

Figure 2:
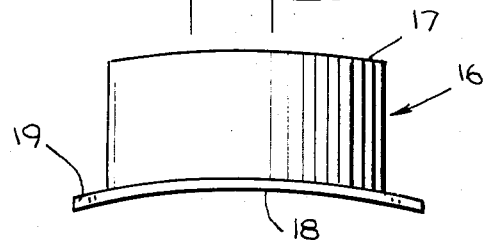
FIG. 2 is a sectional view of an artificial plug utilized in an embodiment of the present invention.
Figure 3:
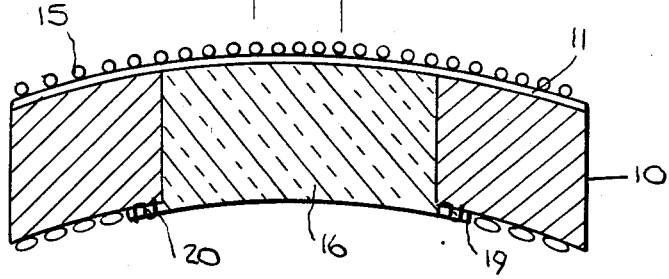
FIG. 3 is a sectional view of the FIG. 1 corneal plug with the FIG. 2 artificial plug seated therein.

A corneal implant in accordance with the invention also includes an optically clear artificial plug 16 represented in FIG. 2 and having dimensions to fit the bore and disposed in the bore as represented in FIG. 3. The artificial plug 16 has a thickness substantially equal to the thickness of the corneal implant, for example, 0.5 mm and a diameter of, for example, 6 to 7 mm. The artificial plug preferably is made of silicone rubber, Hema, or any other suitable optically clear inert material which is compatible with the corneal plug and with the other portions of the patient's eye.

The bore 13 of the corneal plug 10 is a central bore and the artificial plug 16 has a curved anterior surface 17 corresponding to the shape of Bowman's membrane at the bore. The artificial plug 16 has a posterior surface 18 and has a flange 19 at the posterior surface. The artificial plug is sutured by, for example, sutures 20, through the flange 19 to the corneal plug 10, as represented in FIG. 3. The artificial plug 16 could, of course, be maintained in the corneal plug 10 by a suitable mechanical means other than sutures.

A method of making a corneal implant in accordance with the invention comprises removing from a donor eye a corneal plug 10 having Bowman's membrane and a posterior surface 12. The method comprises solidifying the corneal plug preferably by freezing the corneal plug and cutting a bore 13 in the solidified corneal plug from the posterior surface 12 substantially to Bowman's membrane 11. The step of cutting a bore in the solidified corneal plug 10 preferably comprises turning the solidified corneal plug on a lathe in accordance with techniques known in the art.

The method also includes the step of disposing in the bore 13 of the solidified corneal plug 10 an optically clear artificial plug 16 having dimensions to fit the bore. The method further includes the step of returning the solidified corneal plug 10 to its unsolidified state and the step of attaching the artificial plug 16 to the corneal plug 10, preferably by suturing.

The method also includes the step of implanting the corneal plug with the artificial plug therein in the eye of a patient, preferably the same donor eye from which the corneal plug 10 initially was removed.

According to the invention, therefore, a corneal plug 10 is cut from the central corneal portion of a patient's eye, as is usually done in the case of a corneal transplant from a different donor eye. Instead of using a different donor plug, however, preferably the same plug 10 which is cut from the afflicted eye is used in the unique manner described. The plug 10 which is cut from the afflicted eye is frozen solid. It is then placed on a lathe suitable for the purpose and a blind bore 13 is cut from the posterior toward the anterior surface of the plug. The bore is made through the central portion of the corneal plug 10 up to but not through Bowman's membrane 11 located at the anterior surface of the plug. Bowman's membrane is maintained fully intact and provides the required sealing in the region of the bore. An artificial plug 16 having a size and shape fitting the bore 13 in the corneal plug 10 is then inserted into the bore 13 and may be maintained therein either by suturing or by some mechanical locking means, which may, for example, be in the shape of a flange or other projections extending from the artificial plug radially outwardly into the surrounding tissue of the corneal plug 10. Preferably, the anterior surface of the transparent artificial plug is slightly curved so as to correspond to the shape of the posterior surface of Bowman's membrane 11 with which it will be in contact. After assembly of the artificial plug 16 with the corneal plug 10, the latter is inserted into the opening in the cornea of the patient's eye.

Figure 4:
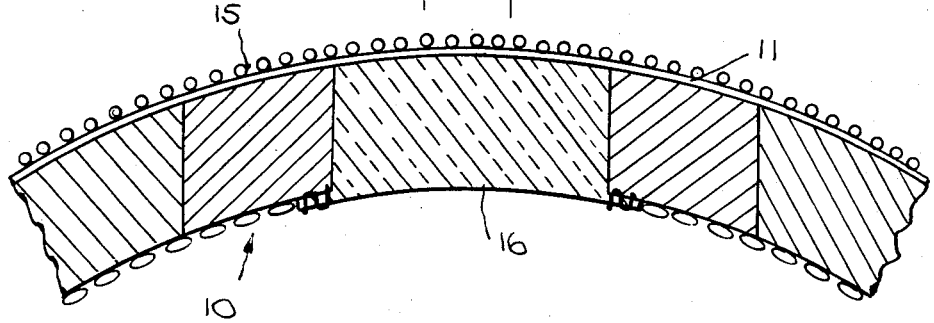
FIG. 4 is a sectional view of the FIG. 3 corneal implant sutured in a cornea which is shown in fragmentary view.

After reinsertion of the corneal plug with the artificial plug therein into the opening of the cornea from which it was initially cut, the corneal plug and the cornea are sutured together around the periphery of the implant, as represented in FIG. 4. The tissues of the corneal implant and of the surrounding cornea will thereafter grow together and form a tight seal. Since preferably the patient's own corneal tissue is being reimplanted, the chance of rejection, even in persons suffering from trachoma, is substantially minimized. It will be noted that after the corneal plug is reinserted into the opening in the cornea which was previously cut, fluid pressure within the eye will tend to maintain the artificial plug pressed against Bowman's membrane and thus keep the artificial plug tightly in place.

Figure 5:
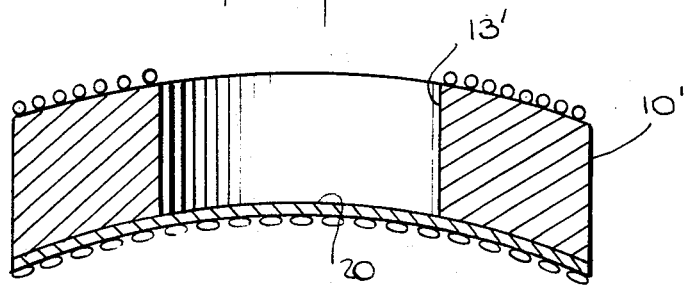
FIG. 5 is a sectional view of a corneal plug according to another embodiment of the invention.
Figure 6:
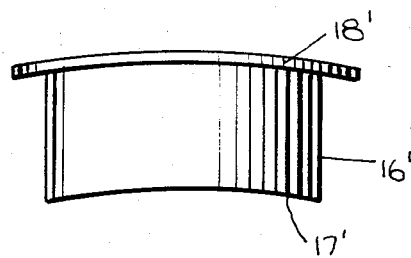
FIG. 6 is a sectional view of an artificial plug utilized in the FIG. 5 embodiment of the invention.

According to another embodiment of the invention, the plug 10' represented in FIG. 5, after it is frozen solid, has a blind bore 13' cut from the anterior toward the posterior surface of the plug. The bore is made through the central portion of the corneal plug 10' up to but not through Descemet's membrane 20 located at the posterior surface of the plug. Descemet's membrane is maintained fully intact and provides the required sealing in the region of the bore. An artificial plug 16' having a size and shape fitting the bore 13' is then inserted and maintained therein substantially in the same manner as previously described with reference to FIGS. 2 through 4. Of course, plug 16' has a surface 17' which is concave so as to correspond to the shape of membrane 20, and another surface 18' which is preferably convex so as to corespond generally to the curvature of the anterior surface of the corneal plug 10'.

It is further contemplated that in those cases where both the Bowman's membrane as well as the Descemet's membrane of a patient are cloudy due to disease, the bore 13 may be cut entirely through both such membranes. A similar healthy membrane, removed from an animal's eye, may then be sutured to the corneal plug in position to cover the anterior surface of the latter, including the bore 13 and resulting in a corneal plug such as represented in FIG. 1.

According to the present invention, therefore, a diseased and/or injured, and, therefore, no longer transparent, cornea can have all or a portion thereof surgically removed, corrected and reimplanted in the same patient so as to overcome the problems present with currently known procedures and corneal implants. It will be understood, of course, that in the event an optical assist rather than a mere transparent window is required, the artificial plug could be shaped in the form of a lens with optical, for example, magnification, characteristics. The corneal implant may, of course, be implanted in a patient's eye after having been initially removed from a donor eye other than the eye of the patient in whose eye it is being implanted so long as the donor eye and the patient's eye in which the corneal plug is being implanted are compatible.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A corneal implant comprising:

a corneal plug removed from a donor eye and having a posterior surface and an anterior surface spaced from said posterior surface, a membrane covering one of said surfaces, and a bore therein extending substantially to said membrane from the other of said surfaces; and an optically clear artificial plug having dimensions to fit said bore and disposed in said bore.

2. A corneal implant in accordance with claim 1, in which said membrane is Bowman's membrane covering said anterior surface of said plug.

3. A corneal implant in accordance with claim 1, in which said membrane is Descemet's membrane covering said posterior surface of said plug.

4. A corneal implant in accordance with claim 1, in which said membrane is a membrane taken from the cornea of an animal and joined to said corneal plug.

5. A corneal implant in accordance with claim 1 in whcih said bore is a central bore in said corneal plug.

6. A corneal implant in accordance with claim 1 in which said artificial plug has a curved anterior surface corresponding to the shape of Bowman's membrane covering said bore.

7. A corneal implant in accordance with claim 1 in which said artificial plug has a posterior surface and a flange in the region of said posterior surface thereof.

8. A corneal implant in accordance with claim 1 in which said artificial plug is sutured to said corneal plug.

9. A corneal implant in accordance with claim 1 in which said artificial plug is transparent rubber.

10. A corneal implant in accordance with claim 1 in which said artificial plug is transparent plastic.

11. A corneal implant in accordance with claim 1 in which said artificial plug is shaped to exhibit the optical properties of a lens.

12. A corneal implant in accordance with claim 1 in which said donor eye is the afflicted eye of the patient who is to receive the corneal implant.

13. A method of making a corneal implant comprising:

removing from a patient's eye a corneal plug having a posterior surface and an anterior surface and a membrane covering one of said surfaces;

solidifying said corneal plug;

cutting a bore in said solidified corneal plug from the other of said surfaces substantially to said membrane;

disposing in said bore of said solidified corneal plug an optically clear artificial plug having dimensions to fit said bore; and attaching said artificial plug to said corneal plug.

14. A method in accordance with claim 13 in which the step of solidifying said corneal plug comprises freezing said corneal plug.

15. A method in accordance with claim 13 in which the step of cutting a bore in said solidified corneal plug comprises turning said solidified corneal plug on a lathe.

16. A method in accordance with claim 13 which comprises the step of returning said solidified corneal plug to its unsolidified state.

17. A method in accordance with claim 13 in which the step of attaching said artificial plug to said corneal plug comprises suturing said artificial plug to said corneal plug.

18. A method in accordance with claim 13 which comprises implanting said corneal plug with said artificial plug therein in the same patient's eye.

19. A method in accordance with claim 13 in which said membrane is Bowman's membrane.

20. A method in accordance with claim 13 in which said membrane is Descemet's membrane.

21. A method in accordance with claim 13 which comprises replacing said membrane with a membrane removed from the eye of an animal prior to solidifying said corneal plug.

* * * * *